(12) United States Patent
Hettel et al.

(10) Patent No.: US 12,304,510 B2
(45) Date of Patent: May 20, 2025

(54) SYSTEM FOR TESTING A DRIVER ASSISTANCE SYSTEM OF A VEHICLE

(71) Applicant: AVL LIST GMBH, Graz (AT)

(72) Inventors: Rolf Hettel, Hockenheim (DE); Tobias Düser, Bühl (DE)

(73) Assignee: AVL LIST GMBH, Graz (AT)

( * ) Notice: Subject to any disclaimer, the term of this patent is extended or adjusted under 35 U.S.C. 154(b) by 85 days.

(21) Appl. No.: 18/002,087

(22) PCT Filed: Jun. 15, 2021

(86) PCT No.: PCT/AT2021/060203
§ 371 (c)(1),
(2) Date: Dec. 16, 2022

(87) PCT Pub. No.: WO2021/253063
PCT Pub. Date: Dec. 23, 2021

(65) Prior Publication Data
US 2023/0219584 A1    Jul. 13, 2023

(30) Foreign Application Priority Data
Jun. 16, 2020 (AT) ............................. A 50515/2020

(51) Int. Cl.
*B60W 50/04* (2006.01)
*B60W 40/08* (2012.01)
*G01M 17/007* (2006.01)

(52) U.S. Cl.
CPC ............ *B60W 50/04* (2013.01); *B60W 40/08* (2013.01); *G01M 17/007* (2013.01);
(Continued)

(58) Field of Classification Search
CPC .. B60W 40/08; B60W 50/04; B60W 2540/22; B60W 2540/24; G01M 17/007;
(Continued)

(56) References Cited

U.S. PATENT DOCUMENTS

| 10,228,693 B2 | 3/2019 | Micks et al. |
| 10,399,565 B2 | 9/2019 | Posch et al. |

(Continued)

FOREIGN PATENT DOCUMENTS

| CN | 101041355 | 9/2007 |
| CN | 103209876 | 7/2013 |

(Continued)

OTHER PUBLICATIONS

International Search Report and Written Opinion for International (PCT) Patent Application No. PCT/AT2021/060203, dated Oct. 14, 2021, 9 pages.

(Continued)

*Primary Examiner* — Justin S Lee
(74) *Attorney, Agent, or Firm* — Sheridan Ross P.C.

(57) ABSTRACT

The invention relates to a system for testing a driver assistance system of a vehicle, where the driver assistance system has at least one interior sensor and is designed to process sensor signals of the at least one interior sensor for monitoring a driver of the vehicle, the system comprising: simulation means for simulating at least one physical property of the driver which characterizes a physiological condition of the driver, in particular the driver's attentiveness, activity, fatigue, mood, state of health, and/or drug influence, and is able to be detected by the at least one interior sensor such that it can generate sensor signals as a function of the at least one simulated physical property; and an interface which interacts with the driver assistance system such that sensor signals are provided the driver assistance system as a function of the at least one simulated physical property. The invention further relates to a corresponding method.

16 Claims, 5 Drawing Sheets

(52) U.S. Cl.
CPC ... *B60W 2540/22* (2013.01); *B60W 2540/221* (2020.02); *B60W 2540/223* (2020.02); *B60W 2540/229* (2020.02); *B60W 2540/24* (2013.01)

(58) Field of Classification Search
CPC .... G06V 20/597; G06V 40/20; G06V 40/168; G06V 40/174; G06V 40/193; G06V 40/16; G06V 40/161; G06V 40/172; G06V 40/179
See application file for complete search history.

(56) References Cited

U.S. PATENT DOCUMENTS

| | | | |
|---|---|---|---|
| 10,482,003 | B1 | 11/2019 | Bondor et al. |
| 10,636,295 | B1 | 4/2020 | Kim et al. |
| 10,913,455 | B2 | 2/2021 | Bruns et al. |
| 11,086,318 | B1 | 8/2021 | Davis |
| 11,137,763 | B2 | 10/2021 | Heit et al. |
| 11,397,136 | B2 | 7/2022 | Schyr et al. |
| 11,417,057 | B2 * | 8/2022 | Atsmon ............ G01C 21/3867 |
| 2004/0176936 | A1 * | 9/2004 | Ohtsu ................ G09B 19/167 |
| | | | 703/8 |
| 2007/0063854 | A1 | 3/2007 | Zhang et al. |
| 2007/0182529 | A1 | 8/2007 | Dobler et al. |
| 2011/0313740 | A1 * | 12/2011 | Ikeda ..................... G05B 17/02 |
| | | | 703/2 |
| 2012/0135382 | A1 | 5/2012 | Winston et al. |
| 2013/0238166 | A1 | 9/2013 | Breu et al. |
| 2015/0105936 | A1 | 4/2015 | Grineenval et al. |
| 2016/0171133 | A1 * | 6/2016 | Pfister ................ G01M 17/007 |
| | | | 703/8 |
| 2016/0210382 | A1 | 7/2016 | Alaniz et al. |
| 2016/0280233 | A1 | 9/2016 | Priller |
| 2016/0379091 | A1 | 12/2016 | Lin |
| 2017/0132117 | A1 | 5/2017 | Stefan et al. |
| 2017/0270236 | A1 | 9/2017 | Yamaura et al. |
| 2017/0278402 | A1 | 9/2017 | Yalla et al. |
| 2017/0286570 | A1 * | 10/2017 | Kim ..................... G06F 11/3688 |
| 2017/0355377 | A1 * | 12/2017 | Vijaya Kumar .. B60W 50/0098 |
| 2018/0060467 | A1 | 3/2018 | Schulte et al. |
| 2018/0079425 | A1 | 3/2018 | Fleck et al. |
| 2018/0275658 | A1 | 9/2018 | Iandola et al. |
| 2018/0339706 | A1 * | 11/2018 | Biondo ................. B60W 50/10 |
| 2019/0047588 | A1 * | 2/2019 | Yabuuchi ............. G06V 20/597 |
| 2019/0111933 | A1 | 4/2019 | Schoeggl et al. |
| 2019/0195734 | A1 * | 6/2019 | Breton ................. F02B 77/084 |
| 2020/0209874 | A1 | 7/2020 | Chen et al. |
| 2020/0216078 | A1 * | 7/2020 | Katz ................... G01C 21/3697 |
| 2021/0237743 | A1 * | 8/2021 | Boström ............... B60W 40/08 |
| 2021/0291839 | A1 * | 9/2021 | Hutchings ................ A61B 5/18 |
| 2023/0043713 | A1 * | 2/2023 | Sakurai ................. B60W 50/14 |
| 2023/0214712 | A1 * | 7/2023 | Furlan .................... G07C 5/008 |
| | | | 706/41 |

FOREIGN PATENT DOCUMENTS

| | | | |
|---|---|---|---|
| CN | 105718065 | | 6/2016 |
| CN | 108646586 | | 10/2018 |
| CN | 108681264 | | 10/2018 |
| CN | 212579772 U | * | 2/2021 |
| CN | 110949396 B | * | 11/2021 ............ B60W 40/08 |
| DE | 4200694 | | 7/1993 |
| DE | 19614061 | | 10/1996 |
| DE | 102007031040 | | 1/2009 |
| DE | 102007043910 | | 3/2009 |
| DE | 102008002699 | | 12/2009 |
| DE | 102009028767 | | 2/2011 |
| DE | 102010029922 | | 12/2011 |
| DE | 102011000409 | | 8/2012 |
| DE | 102011087781 | | 6/2013 |
| DE | 102011088807 | | 6/2013 |
| DE | 102011121537 | | 6/2013 |
| DE | 102012001666 | | 8/2013 |
| DE | 102012002333 | | 8/2013 |
| DE | 102012201896 | | 8/2013 |
| DE | 102013200116 | | 7/2014 |
| DE | 102014118625 | | 6/2016 |
| DE | 102015104890 | | 10/2016 |
| DE | 102018200011 | | 7/2019 |
| DE | 102018205804 | | 10/2019 |
| DE | 102019105363 | | 10/2020 |
| DE | 102019206049 | | 10/2020 |
| DE | 102019206052 | | 10/2020 |
| EP | 0836945 | | 4/1998 |
| EP | 2284057 | | 2/2011 |
| EP | 3438901 | | 2/2019 |
| EP | 3745381 | | 12/2020 |
| EP | 3745382 | | 12/2020 |
| JP | 2008-123197 | | 5/2008 |
| JP | 2008-146332 | | 6/2008 |
| JP | 2015-516623 | | 6/2015 |
| JP | 2016-531044 | | 10/2016 |
| JP | 2017-105453 | | 6/2017 |
| JP | 2017-173309 | | 9/2017 |
| WO | WO 2004/045895 | | 6/2004 |
| WO | WO 2012/088635 | | 7/2012 |
| WO | WO 2013/060507 | | 5/2013 |
| WO | WO 2013/174974 | | 11/2013 |
| WO | WO 2015/032508 | | 3/2015 |
| WO | WO 2017/167790 | | 10/2017 |
| WO | WO 2017/210222 | | 12/2017 |
| WO | WO 2019/108985 | | 6/2019 |
| WO | WO 2019/119012 | | 6/2019 |
| WO | WO 2019/201400 | | 10/2019 |
| WO | WO-2019220436 A2 * | 11/2019 ............ B60W 40/08 |
| WO | WO 2020/083996 | | 4/2020 |

OTHER PUBLICATIONS

English Translation of the International Search Report for International (PCT) Patent Application No. PCT/ AT2021/060203, dated Oct. 14, 2021, 2 pages.

"ASAM OpenScenario: User Guide," ASAM e.V., last updated Mar. 16, 2020, Version 1.0.0, 54 pages.

Bako Rajaonah et al: "Trust and the use of adaptive cruise control: a study of a cut-in situation", Cognition, Technology & Work, Springer-Verlag, LO, vol. 8, No. 2, Mar. 14, 2006; pp. 146-155.

Elrofai et al. "Scenario-Based Safety Validation of Connected and Automated Driving," StreetWise, TNO, Jul. 1, 2018, pp. 1-28 [Retrieved online from: publications.tno.nl/publication/34626550/AyT8Zc/TNO-2018-streetwise.pdf].

Erdogan et al. "Real-World Maneuver Extraction for Autonomous Vehicle Validation: A Comparative Study," IEEE, 2019 IEEE Intelligent Vehicles Symposium (IV), Jun. 9-12, 2019, Paris, France, pp. 267-272.

MSC Software "Virtual Test Drive (VTD): Webinar-Leverage Simulation to Achieve Safety for Autonomous Vehicles," YouTube, Jun. 10, 2019, 39 pages [retrieved online from: www.youtube.com/watch?v=NksyrGA8Cek].

Vernaza et al. "Simul-A2: Agent-based Simulator for evaluate ADA Systems," 17th International Conference on Information Fusion (Fusion), International, Jul. 7, 2014, 7 pages.

* cited by examiner

SYSTEM FOR TESTING A DRIVER ASSISTANCE SYSTEM OF A VEHICLE

CROSS REFERENCE TO RELATED APPLICATIONS

This application is a national stage application under 35 U.S.C. 371 and claims the benefit of PCT Application No. PCT/AT2021/060203 having an international filing date of 15 Jun. 2021, which designated the United States, which PCT application claimed the benefit of Austria Patent Application No. A50515/2020 filed 16 Jun. 2020, the disclosures of each of which are incorporated herein by reference in their entireties.

FIELD OF THE INVENTION

The invention relates to a system for testing a driver assistance system of a vehicle, wherein the driver assistance system comprises at least one interior sensor and is designed to process sensor signals of the at least one interior sensor for monitoring a driver of the vehicle.

BACKGROUND OF THE INVENTION

Vehicles capable of automated or highly automated driving through the use of driver assistance systems, in particular vehicles of automation levels 3 to 5 (see e.g., SAE Standard J3016), require monitoring of the driver's attentiveness in order to ensure being able to assume guidance of the vehicle at short notice.

Driver assistance systems are increasingly being used in modern motor vehicles in order to increase active road safety. For example, adaptive automatic vehicle interval control, also known as Adaptive Cruise Control (ACC), adaptively adjusts a desired speed selected by a driver to the distance from a vehicle ahead. Further examples of driver assistance systems are ACC stop-and-go systems which, in addition to ACC, effect the automatic further travel of the vehicle in a traffic jam or stationary traffic, lane departure warning or lane assist systems which automatically keep the vehicle in the vehicle lane, and pre-crash systems which for example prepare or initiate braking in the event of a possible collision in order to draw the kinetic energy out of the vehicle as well as potentially initiate further measures should a collision be unavoidable.

SUMMARY OF THE INVENTION

These driver assistance systems expect that the driver is in an attentive state; in other words, not overtired or inattentive.

To increase safety, driver assistance systems are therefore increasingly being equipped with devices which determine the attentiveness or physiological condition of the driver.

Should it be detected that the driver is not in good physiological condition, a warning can for example be issued or an appropriate response of the driver assistance systems initiated. Doing so ensures that the driver pays attention to the act of driving.

Document EP 2 284 057 relates to a method for adapting one or more parameters of a driver assistance system assisting the driver of a motor vehicle which comprises the following steps:

determining the driver's current viewing direction by means of gaze direction detection, determining the time period during which the driver is not looking at the road from the current viewing direction, and adapting the parameter or parameters of the driver assistance system if the time period determined exceeds a predefined critical time value.

The task of the invention is that of enabling an optimization of driver assistance systems. In particular a task of the invention is providing testing of driver assistance systems such as, for example, the previously cited vehicle driver assistance systems and particularly those for vehicles at automation levels of 3 to 5.

This task is solved by a system for testing a driver assistance system and a method for testing a driver assistance system in accordance with the independent claims. Further embodiments are claimed in the dependent claims.

A first aspect of the invention relates to a system for testing a driver assistance system of a vehicle, wherein the driver assistance system has at least one interior sensor and is designed to process sensor signals of the at least one interior sensor for monitoring a driver of the vehicle, the system comprising:

simulation means for simulating at least one physical property of the driver characterizing a physiological condition of the driver, in particular the driver's attentiveness, activity, fatigue, mood, state of health and/or drug influence, and being detectable by the at least one interior sensor such that it can generate sensor signals as a function of the at least one simulated physical property; and an interface which interacts with the driver assistance system such that sensor signals are provided the driver assistance system as a function of the at least one simulated physical property.

A second aspect of the invention relates to a method for testing a driver assistance system of a vehicle, particularly by means of a system according to one of claims 1 to 15, wherein the driver assistance system has at least one interior sensor and is designed to process sensor signals of the at least one interior sensor for monitoring a driver of the vehicle, wherein at least one physical property of the driver is simulated which characterizes a physiological condition of the driver, in particular attentiveness, activity, fatigue, mood, state of health and/or drug influence, and is able to be detected by the at least one interior sensor such that it can generate sensor signals as a function of the at least one simulated physical property and the sensor signals are provided the driver assistance system as a function of the at least one simulated physical property.

Further aspects of the invention relate to a computer program containing instructions which, when run on a computer, prompt it to do execute the steps of a method according to the second aspect of the invention, and to a computer-readable medium on which such a computer program is stored.

The invention is based on the approach of testing driver assistance systems comprising at least one interior sensor for driver monitoring by means of objectified and reproducible input.

The inventive system comprises simulation means to that end which are configured so as to simulate the physical properties of a driver able to be detected by the at least one interior sensor. Sensor signals of the interior sensors are provided to the driver assistance system via an interface, in particular a stimulation device. Preferably, the stimulation device thereby emulates a driver so that the at least one interior sensor outputs sensor data as if it were observing a real driver.

Alternatively, sensor data can also be generated by so-called injection to a sensor chip of the interior sensor or also by direct injection of simulated sensor data to the driver assistance system.

The functionality of the driver assistance system with regard to the interior sensor can thereby be tested by means of the simulated data. Alternatively or additionally, the interior sensor or its sensor chip can also be tested. In the latter case, signal disturbances generated by a physical signal recording unit, in particular a camera's optics, are factored out when testing the driver assistance system and/or the sensor chip. Additionally, however, artificial signal degradations or disturbances can also be simulated in order to learn how the sensor chip and/or the driver assistance system can handle that.

By simulating the at least one physical property of the driver, input to the interior sensor and/or the driver assistance system can be controlled precisely and reproducibly. In most cases, this would be very difficult with an actual person. While attentiveness and activity can still be mimicked to a limited extent by an actual person, an actual person cannot conjure up fatigue, mood, state of health and/or drug influence on command. Furthermore, when in use in actual traffic, it would be extremely dangerous for a real driver to focus on not paying attention in order to test a response of a driver assistance system.

With the system and method according to the invention, a plurality of a driver's physiological conditions can be reproduced and the driver assistance system can then be tested on the basis of same. Both the driver as a whole including his gestures, facial expressions, posture and contact with the interior of the vehicle, as well as only parts of the driver, for example only his face or only the position of his hand on the steering wheel, can thereby be reproduced.

Preferably, the simulation means is designed to generate signals, particularly sensor signals, which depict information from the perspective of the vehicle's interior sensor. Firstly important here is for the signals to depict the physical properties of the driver within the field of view of the interior sensor. Also of importance is the perspective of the driver's physical property depiction. Lastly of importance is the position of the individual body parts as well as the proportions of the depicted body and the individually depicted body parts.

In one advantageous embodiment of the system, the interface is a stimulation device which is configured to stimulate the interior sensor on the basis of the at least one simulated physical property. In this case, the driver assistance system can be tested as a whole, as installed in a vehicle. Modifications to the sensor or a data connection between the interior sensor and a data processing unit of the driver assistance system are not necessary. Although with that said, the interior sensor can also be arranged external of a vehicle and stimulated there. The invention also enables testing the driver assistance system as a whole without a vehicle.

In a further advantageous embodiment of the system, the stimulation device is configured to generate a response signal for reception by the at least one interior sensor based on a signal emitted by the at least one interior sensor, wherein the response signal is generated based on the at least one simulated physical property, and wherein the driver is preferably emulated when generating the response signal. This advantageous embodiment also enables the testing of driver assistance systems having interior sensors which emit a scanning signal. These can for example be ultrasonic sensors or even photodiodes.

In a further advantageous embodiment, the stimulation device is selected from the following group of stimulation devices: a display screen 6a, 6b, 6e, a loudspeaker, a heart rate stimulator, a hand emulator, a weight emulator. Selecting the appropriate stimulation device or devices can enable the optimal stimulation of the interior sensor or sensors.

In a further advantageous embodiment of the system, the stimulation device is designed as a structural unit preferably incorporating a housing and with an interior sensor able to be accommodated within the structural unit, wherein the interior sensor corresponds in particular functionally and/or structurally to the at least one interior sensor of the driver assistance system to be tested or is the interior sensor of the driver assistance system to be tested, and wherein the stimulation device is connectable to the driver assistance system to be tested for the purpose of signal transmission in order for a sensor signal to be transmitted from the stimulation device to the driver assistance system. This advantageous embodiment enables the interior sensor together with the stimulation device to be positioned externally of the vehicle, in particular at a location external of the actual test bench. This can thereby prevent interference in the stimulation of the interior sensor or sensors by a test bench operation of the vehicle or the driver assistance system itself.

In a further advantageous embodiment, the at least one interior sensor is arranged and/or installed in a component, in particular a component of the vehicle, preferably a dashboard or steering wheel of the vehicle, and this component can be received by the stimulation device. According to this exemplary embodiment, the interior sensor of the driver assistance system does not need to be removed from its environment in normal operation, whereby possible interactions can be taken into account when testing the driver assistance system within the environment.

In a further advantageous embodiment of the system, the stimulation device is configured to be mounted on a driver's seat and/or a gear selector lever and/or steering wheel. The stimulation of the interior sensor of the driver assistance system can thereby be realized in the actual vehicle and thus also in real vehicle operation or driving operation on a test bench.

In a further advantageous embodiment of the system, the stimulation means is configured to generate raw sensor data and the interface is configured to inject the raw sensor data into a sensor chip of the interior sensor, in particular a perception chip of a camera. This embodiment enables dispensing with the driver assistance system regardless of a sensor's pick-up element; i.e. that part of the sensor which converts measurement signals into electrical, in particular analog, signals, the optics in the case of a camera. On the one hand, the sensor chip or respectively the interaction of the sensor chip with the driver assistance system can thereby be tested without pick-up element interference and, on the other hand, pick-up element interference can also be selectively simulated and monitored in terms of how the driver assistance system, or the perception chip of the interior sensor respectively, processes same.

In a further advantageous embodiment of the system, the at least one physical property is selected from among the following group of properties: biometric properties, seated position, posture, position of the head, viewing direction, facial expression, occluded field of view, in particular due to a hat, mask or sunglasses, weight, blood pressure, heart rate, eye movement, eyelid movement, pupil size or driver blood alcohol concentration.

In a further advantageous embodiment, the at least one interior sensor is selected from among the following group of sensors: camera, in particular stereoscopic camera, preferably infrared camera, capacitive sensor, photodiode, mechanical force sensor or resistive sensor, steering angle sensor, steering torque sensor or microphone.

In a further advantageous embodiment of the system, the physical property additionally characterizes driver identity. This thereby enables the individual testing of the driver assistance system in relation to a driver. In addition, an identification function of a vehicle system can be tested.

In one advantageous embodiment of the test bench, the stimulation device is connected to the test bench solely by means of a signal transmission connection, preferably by means of a cable, a bus system, in particular a field bus, and/or by means of a wireless connection. This enables the stimulation device and also the corresponding interior sensors of the driver assistance system to be arranged external of the test bench.

In one advantageous embodiment of the method, the at least one physical property is simulated by means of a driver model. Using a model of the driver enables simulating a wide variety of the driver's physiological conditions or the physical properties associated with same.

In a further advantageous embodiment of the method, the driver model comprises a driver animation, in particular a 3D animation, which is able to emulate physiological conditions. Preferably, the model is trained on the basis of real data.

In a further advantageous embodiment of the method, the simulation is based on recorded data of an actual person, in particular video data of the person, provided one or more physiological conditions within the data are known. This embodiment is particularly simple to implement and enables testing without establishing or respectively training a driver model.

In a further advantageous embodiment, the driver model comprises a driver animation, in particular a 3D animation, able to emulate physiological conditions. This thereby enables particularly realistic testing of in particular driver assistance systems having a camera as an interior sensor.

In a further advantageous embodiment of the method, the driver model is controlled on the basis of data determined from a real person, in particular in real time. This thereby enables the particularly realistic simulating of the person's physiological conditions or physical properties.

In a further advantageous embodiment of the method, the driver assistance system, or the vehicle using the driver assistance system, is operated on the basis of the sensor signals, in particular on a test bench or in actual vehicle operation.

In a further advantageous embodiment of the method, an activity of the driver assistance system is monitored and an evaluation of a function of the driver assistance system is preferably made on the basis of the activity. An evaluation of a driver assistance system preferably ensues on the basis of reference data or a reference driver or reference driver assistance system respectively. This thereby enables the qualitative assessment of the driver assistance system or its properties respectively.

In a further advantageous embodiment of the method, the sensor signals provided for driver assistance system processing are generated on the basis of at least one simulated physical property instead of being generated by the at least one interior sensor. This thereby enables the direct testing of the driver assistance system. The actual interior sensor is bypassed.

In a further advantageous embodiment of the method, signal transmission of the at least one interior sensor of a driver assistance system is prevented.

In a further advantageous embodiment of the method, raw sensor data is generated on the basis of the at least one physical property and injected into a sensor chip of the at least one interior sensor such that it provides the sensor signals. As explained above, the driver assistance system can thereby be tested without the pick-up element of the interior sensor.

In a further advantageous embodiment of the method, the at least one interior sensor is stimulated on the basis of the at least one simulated physical property such that it provides the sensor signals. As explained above, this thereby enables testing the driver assistance system together with the entire interior sensor including the pick-up element.

BRIEF DESCRIPTION OF THE DRAWINGS

Further features and advantages derive from the following description of exemplary embodiments in conjunction with the figures. Shown therein at least partly schematically:

FIG. 1 shows a first exemplary embodiment of a system 1 for testing a driver assistance system 2 which is installed in a vehicle 3.

Figure 1:
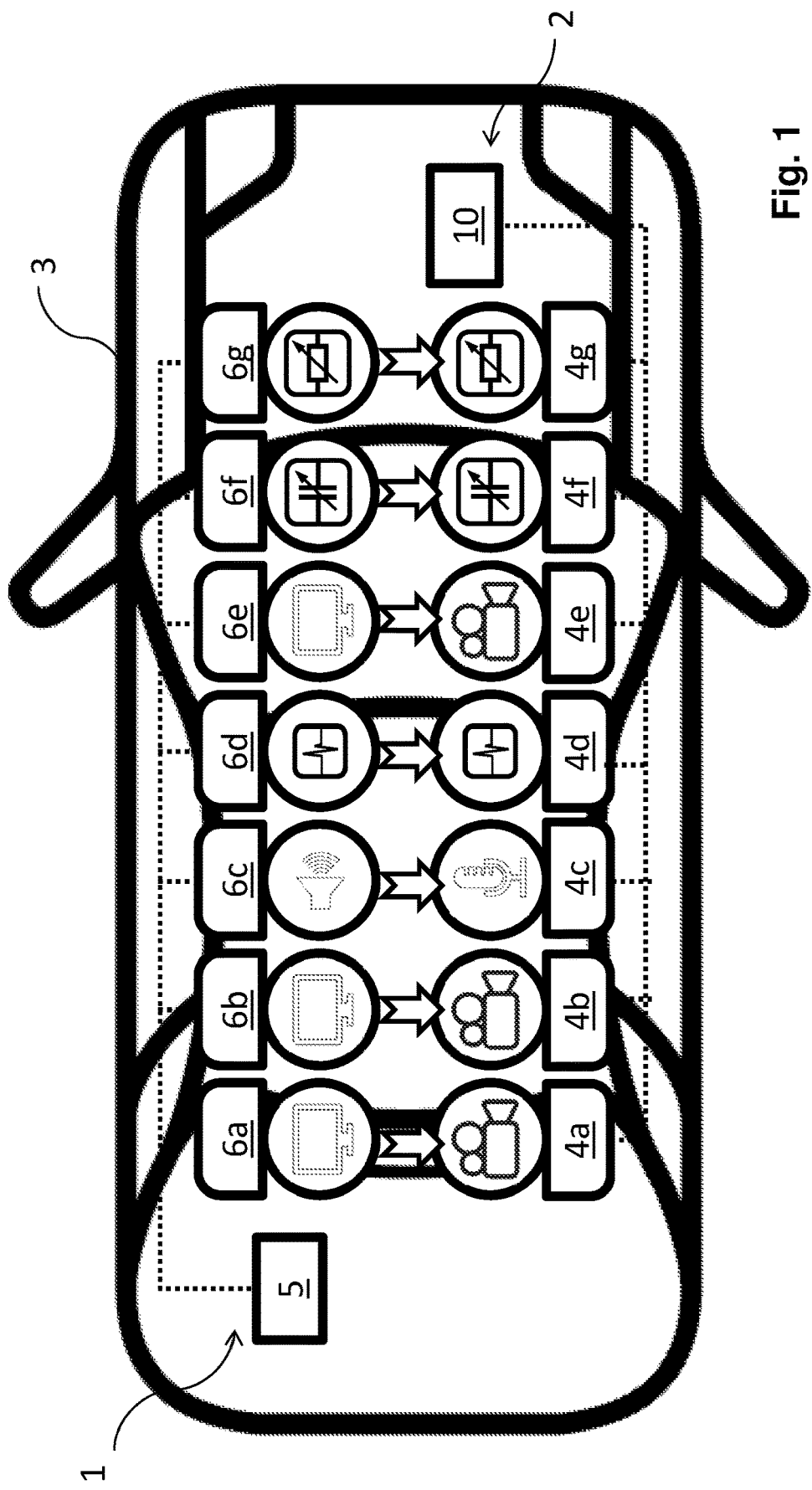
FIG. 1 a first exemplary embodiment of a system for testing a driver assistance system.

A simulation means 5, in particular a computing unit of the system 1, simulates physical properties of a driver characterizing a physiological condition of the driver, in particular his attentiveness, activity, fatigue, mood, state of health and/or the influence of a drug.

DETAILED DESCRIPTION

To that end, the simulation means 5 determines, by means of a driver model, biometric features or respectively properties of the driver, gestures, the driver's seated position, the driver's posture, the position of the driver's head, the driver's viewing direction, the driver's facial expression, any concealment of the driver, in particular due to a hat, mask or sunglasses, the driver's weight, the driver's eyelid movement, the driver's size or driver's blood alcohol concentration as being physical properties.

In the normal case, a physiological condition is characterized not by one of the aforementioned physical properties but by a plurality of these properties.

Driver assistance systems 2 which monitor the driver use the information obtained about the driver's physiological condition to on the one hand ascertain the driver's ability to drive and, on the other hand, to observe the driver's reactions to the vehicle guidance provided by a driver assistance system. One result of a driver being monitored by a driver assistance system 2, for example the lane keeping assist, may be that the driver is prompted to redirect his attention back to what is happening on the road in front of the vehicle 3.

In addition to a computing unit 10, a driver assistance system 2 has various interior sensors. These being for example different cameras 4*a*, 4*b*, 4*e*, in particular stereoscopic cameras, for monitoring different body parts. Thus, of interest to a driver's physiological condition is e.g. the position of his head, the viewing direction or eye position and his facial expression. In order to be able to determine all three parameters, the driver assistance system preferably comprises three stereoscopic cameras 4*a*, 4*b*, 4*e*. A first stereoscopic camera 4*a* captures the head position, a second stereoscopic camera 4*b* captures the viewing direction and a third stereoscopic camera 4*e* captures the facial expression. Furthermore, the driver assistance system 2 preferably has a microphone 4*c* for detecting noise, e.g. driver utterances, a photodiode 4*d* for detecting heart rate, a capacitive sensor 4*f* for detecting the position of the hand on the steering wheel, as well as a mechanical force sensor or resistive sensor 4*g* for detecting the seated position.

The sensor signals generated by the interior sensors 4*a*, 4*b*, 4*c*, 4*d*, 4*e*, 4*f*, 4*g* are evaluated in the computing unit 10 of the driver assistance system 2 and the driver assistance system controls the corresponding functions of the vehicle 3 or the entire vehicle 3 respectively.

A system 1 for testing the driver assistance system 2 checks the quality of the monitoring performed by the driver assistance system 2. To do so, the individual physical properties, which together yield the physiological condition of the driver, are provided to the driver assistance system 2 via suitable interfaces 6*a*, 6*b*, 6*c*, 6*d*, 6*e*, 6*f*, 6*g*.

The system 1 for testing such a driver assistance system 2, which is shown in FIG. 1, comprises appropriate stimulation devices 6*a*, 6*b*, 6*c*, 6*d*, 6*e*, 6*f*, 6*g* in order to stimulate the interior sensors 4*a*, 4*b*, 4*c*, 4*d*, 4*e*, 4*f*, 4*g* according to the simulated physical properties.

This stimulation is in each case indicated in FIG. 1 by arrows.

If the interior sensor is a sensor which initially emits a signal so as to be able to detect a driver's physical property, for example an ultrasonic sensor for detecting distance (not shown), a corresponding stimulation device (not shown) as well as simulation means 5 are also furnished in order to receive the signal and simulate a response signal on the basis of the physical properties on the one hand and then to stimulate the corresponding interior sensor as if the response signal would have occurred as a result of interaction with the driver's body.

In the first exemplary embodiment shown in FIG. 1, the system 1 comprises a first display screen 6*a* for stimulating a first camera 4*a*, wherein the position of the driver's head is displayed on the first display screen. The driver's viewing direction or eye position respectively is correspondingly displayed on the second display screen 6*b* and his facial expression on the third display screen 6*e*. Alternatively, two or all three of these visually perceptible physical properties of the driver can also be displayed by a single display screen and captured by a single camera.

Preferably, the stimulation devices 6*a*, 6*b*, 6*c*, 6*d*, 6*e*, 6*f*, 6*g* are thereby configured so as to be mounted at the location in the vehicle 3 at which the interior sensors 4*a*, 4*b*, 4*c*, 4*d*, 4*e*, 4*f*, 4*g* detect the respective physical property of the driver. It is thereby particularly important for the respective stimulation device 6*a*, 6*b*, 6*c*, 6*d*, 6*e*, 6*f*, 6*g* to be arranged in the field of view of the respective sensor or, respectively, that the physical property of the driver is depicted in the correct perspective of the interior sensor 4*a*, 4*b*, 4*c*, 4*d*, 4*e*, 4*f*, 4*g* and/or at the correct location in the vehicle's interior. This is particularly important in the case of those physical properties captured by the stereoscopic cameras 4*a*, 4*b*, 4*e*.

Further interior sensors can also be provided, these not being shown but which likewise detect a physical property of the driver. Examples of such interior sensors include steering angle sensors which are able to detect driver movement and steering torque sensors which are able to detect force exerted by the driver. Correspondingly, further stimulation devices for these interior sensors can also be provided.

The computing unit 10 of the driver assistance system 2 derives a physiological condition of the driver from the collected data of the sensor signals.

It can moreover be provided for the driver assistance system 2 to determine the identity of the driver.

The physiological condition determined by the driver assistance system 10 can then be compared to the physiological condition simulated by the simulation means 5 of the system 1. Based on this comparison, the quality of the driver assistance system as a whole; i.e. along with all interior sensors, can be evaluated as to the ability to detect a physiological condition of the driver.

The first exemplary embodiment of the system 1 according to FIG. 1 can be used both in the real driving operation of a vehicle 3, in which the vehicle 3 is guided, in particular remotely controlled, by a driver assistance system 2 or by a driver. Further preferably, the system 1 according to the first exemplary embodiment can also be used on a test bench on which driving operation of the vehicle 2 is simulated.

Such a test bench is preferably a vehicle test bench, a hardware-in-the-loop test bench for the driver assistance system 2, a vehicle-in-the-loop test bench for the vehicle 3 or even a driving simulator. Preferably, the test bench 8 is thereby configured so as to enable operation of a motor vehicle's powertrain.

Figure 2:
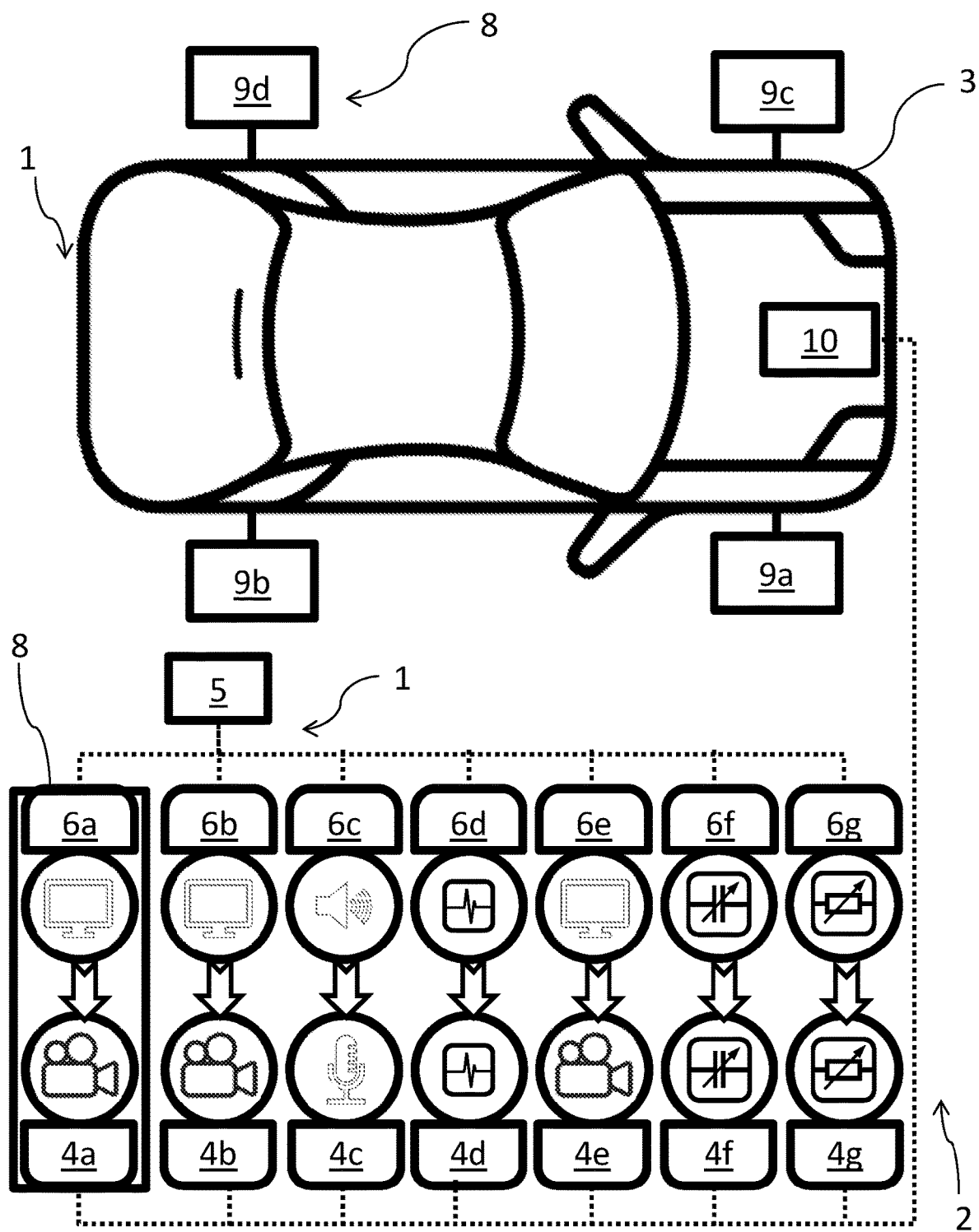
FIG. 2 a second exemplary embodiment of a system for testing a driver assistance system.

A test bench 8 is shown in FIG. 2. Preferably, the test bench 8 comprises four dynamometers 9*a*, 9*b*, 9*c*, 9*d* able to load the wheels or hubs of a vehicle secured to the test bench 8.

The second exemplary embodiment of the system 1 shown in FIG. 2 differs in that the interior sensors 4*a*, 4*b*, 4*c*, 4*d*, 4*e*, 4*f*, 4*g* are not arranged inside the vehicle 3 but rather external of the vehicle 3. Only the computing unit 10 of the driver assistance system 2, which guides the vehicle, is arranged within the vehicle. Correspondingly, the stimulation devices 6*a*, 6*b*, 6*c*, 6*d*, 6*e*, 6*f*, 6*g* are also arranged external of the vehicle 3 in such a way as to be able to interact with the interior 6 and the sensors 4*a*, 4*b*, 4*c*, 4*d*, 4*e*, 4*f*, 4*g* in the manner as described with reference to FIG. 1.

When the respective interior sensor 4*a*, 4*b*, 4*c*, 4*d*, 4*e*, 4*f*, 4*g* is installed in a component of the vehicle, for example in a dashboard or steering wheel or seat, etc., the entire component can also be removed from the vehicle in the second exemplary embodiment in order to stimulate the respective interior sensor 4*a*, 4*b*, 4*c*, 4*d*, 4*e*, 4*f*, 4*g*.

Preferably, the stimulation device 6*a*, 6*b*, 6*c*, 6*d*, 6*e*, 6*f*, 6*g* can be designed as a structural unit which incorporates a housing and in which the respective interior sensor 4*a*, 4*b*, 4*c*, 4*d*, 4*e*, 4*f*, 4*g* can be accommodated. This is depicted in FIG. 2 with respect to the first display screen 6*a* incorporated by a housing 8 in which the first stereoscopic camera 4*a* is likewise arranged.

Arranging the interior sensors 4*a*, 4*b*, 4*c*, 4*d*, 4*e*, 4*f*, 4*g* and the stimulation device 6*a*, 6*b*, 6*c*, 6*d*, 6*e*, 6*f*, 6*g* at a distance from the test bench can minimize interference in the signals acquired by the interior sensors 4*a*, 4*b*, 4*c*, 4*d*, 4*e*, 4*f*, 4*g*. For example, microphone 4*c* does not pick up noise from the test bench 8 or the vehicle 3. Even the housing 8 serves in suppressing possible interior sensor interference or interference in the interaction between stimulation devices 6a, 6b, 6c, 6d, 6e, 6f, 6g and interior sensors 4a, 4b, 4c, 4d, 4e, 4f, 4g respectively.

Preferably, the stimulation devices 6a, 6b, 6c, 6d, 6e, 6f, 6g and interior sensors 4a, 4b, 4c, 4d, 4e, 4f, 4g are thereby arranged in another room and connected to the test bench by means of a connection for signal transmission, preferably by means of a cable of a bus system, in particular a field bus, and/or by means of a wireless connection.

Figure 3:
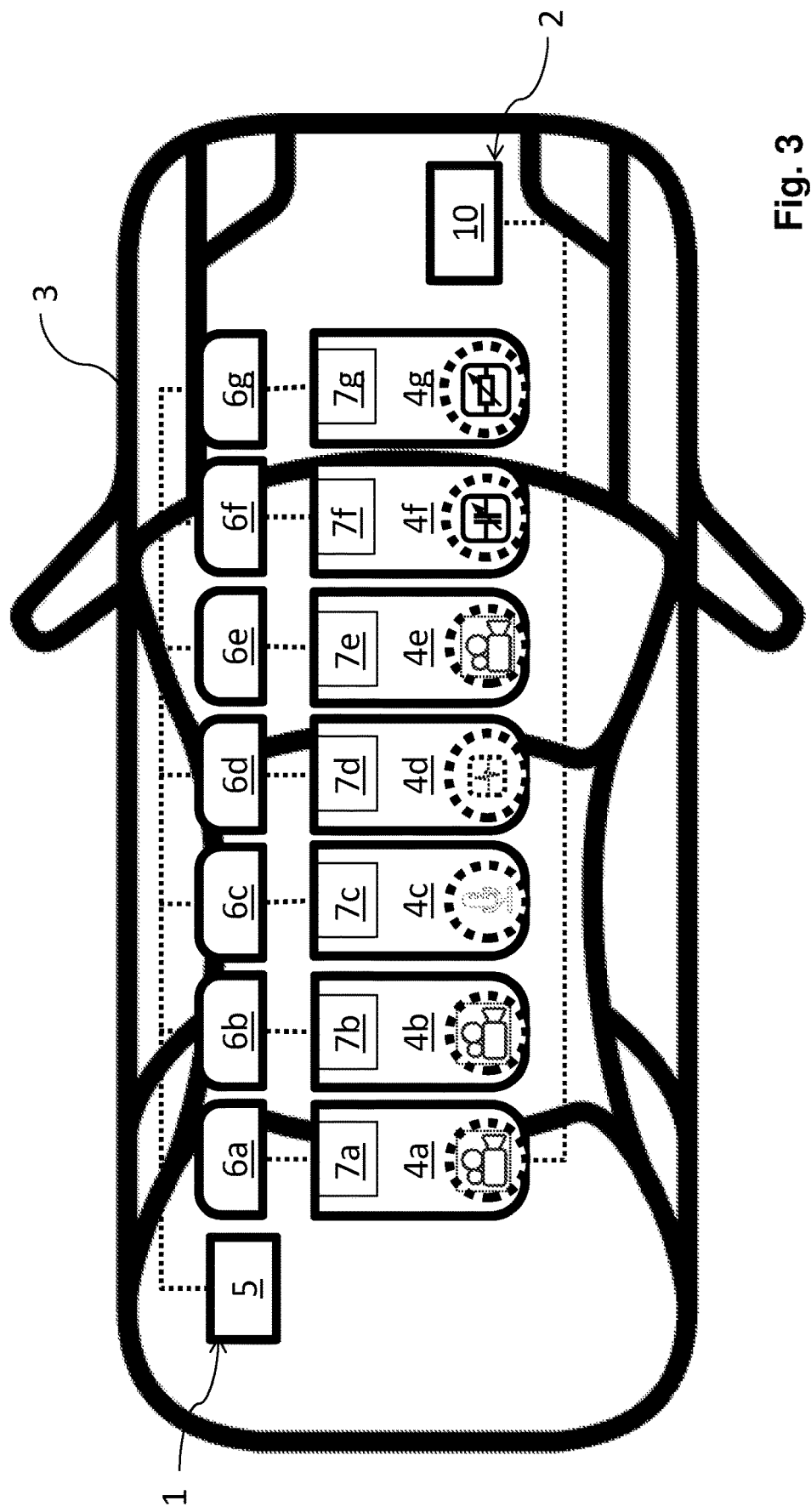
FIG. 3 a third exemplary embodiment of a system for testing a driver assistance system.

FIG. 3 shows a third exemplary embodiment of the inventive system 1. In contrast to the exemplary embodiments of FIG. 1 and FIG. 2, the interfaces 6a, 6b, 6c, 6d, 6e, 6f, 6g in this exemplary embodiment are not stimulation devices but rather data interfaces with which raw sensor data can be fed or respectively injected into the respective sensor chips 7a, 7b, 7c, 7d, 7e, 7f, 7g of the individual interior sensors 4a, 4b, 4c, 4d, 4e, 4f, 4g. To illustrate this, the respective symbols of the interior sensors 4a, 4b, 4c, 4d, 4e, 4f, 4g in FIG. 3 are only encircled by a dotted border.

The sensor chip 7, a respective perception chip 7a, 7b, 7e in the case of the stereoscopic cameras 4a, 4b, 4e, processes the raw sensor data and outputs the corresponding sensor signals which are processed by the computing unit 10 of the driver assistance system 2 and used to guide the vehicle 3.

Figure 4:
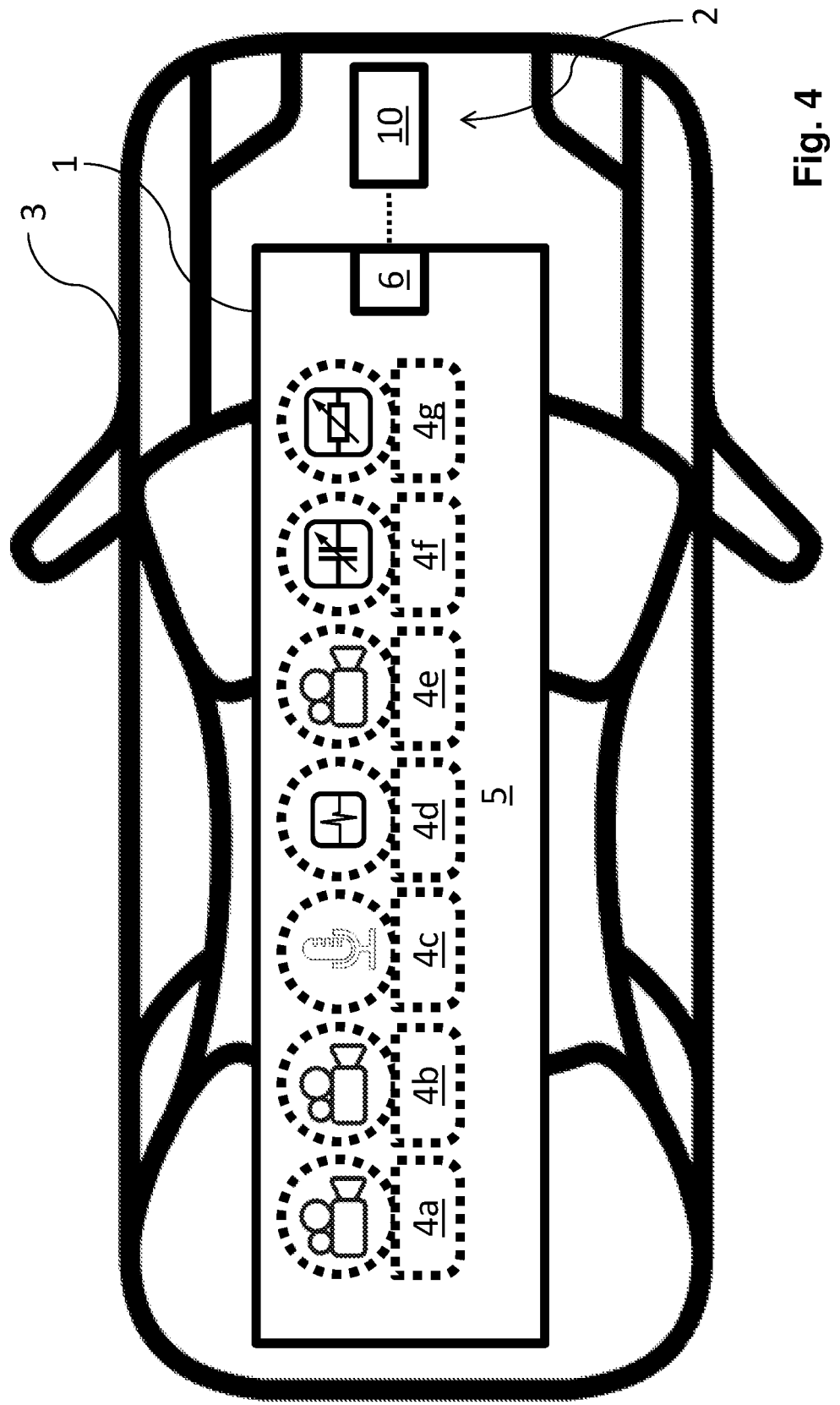
FIG. 4 a fourth exemplary embodiment of a system for testing a driver assistance system.

FIG. 4 shows a fourth exemplary embodiment of the system 1. In contrast to the preceding exemplary embodiments, there is no longer any component of the interior sensors, which is indicated in FIG. 4 by the interior sensor dotting.

Both the input signals, which are elicited by a predetermined physical property of the driver, as well as the function of the interior sensors are completely simulated by the simulation means 5 of the system 1. Via interface 6, the system 1 outputs the sensor signals directly to the computing unit 10 of the driver assistance system 2 which then guides the vehicle 3 on the basis of these sensor signals and any possible further information.

Figure 5:
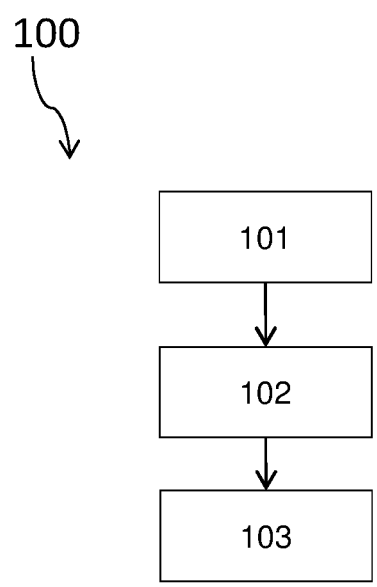
FIG. 5 an exemplary embodiment of a method for testing a driver assistance system.

FIG. 5 shows an exemplary embodiment of a method 100 for testing a driver assistance system 2 of a vehicle 3. In particular, this method is implemented by means of a system 1 as described with reference to the exemplary embodiments of FIGS. 1 to 4.

The method substantially comprises three steps:

In a work step 101, at least one physical property of the driver is simulated 101 which characterizes a physiological condition of the driver, in particular attentiveness, activity, fatigue, mood, state of health and/or drug influence, and which is able to be detected by the at least one interior sensor 4a, 4b, 4c, 4d, 4e, 4f, 4g such that it can generate sensor signals as a function of the at least one simulated physical property.

Preferably, the simulation 101 is thereby based on recorded data of an actual person, particularly video data of the person, for which one or more data points is/are available and physiological conditions are known. Alternatively preferable is for the at least one physical property to be simulated by means of a driver model which is preferably trained on the basis of real data. Further preferably, the driver model comprises an animation which is able to mimic physiological conditions. Further preferably, the driver model is controlled on the basis of data determined in particular in real time from an actual person.

In a second step 102, the driver assistance system 2 provides the sensor signals as a function of the at least one simulated physical property. The driver assistance system 2 or the vehicle using the driver assistance system 2 is operated on a test bench 8 or in real driving operation based on these sensor signals.

In a third step 103, the activity of the driver assistance system 2 is monitored, in particular monitored is which physiological conditions of the driver are detected by the driver assistance system 2. Preferably, the driver assistance system 2 function is evaluated on the basis of this monitoring.

Alternatively, the sensor signals provided for processing by the driver assistance system can be generated on the basis of the at least one simulated physical property instead of being generated by the at least one interior sensor 4a, 4b, 4c, 4d, 4e, 4f, 4g. An animation or the like can be dispensed with in this case. In particular, signal transmission of the at least one interior sensor of a driver assistance system is suppressed in this case.

Further alternatively, raw sensor data can be generated during the simulation on the basis of at least one simulated physical property and injected directly into the sensor chip 7a, 7b, 7c, 7d, 7e, 7f, 7g of the at least one interior sensor 4a, 4b, 4c, 4d, 4e, 4f, 4g so as to provide the sensor signals.

Further alternatively, the at least one interior sensor 4a, 4b, 4c, 4d, 4e, 4f, 4g can be stimulated on the basis of the at least one simulated physical property in such a way as to provide the sensor signals.

Preferably, the method 100 is computer-implemented.

It is to be noted that the exemplary embodiments are only examples which are in no way intended to limit the scope of protection, application and configuration. Rather, the foregoing description is to provide the person skilled in the art with a guideline for implementing at least one exemplary embodiment, whereby various modifications can be made, particularly as regards the function and arrangement of the described components, without departing from the scope of protection resulting from the claims and equivalent combinations of features.

LIST OF REFERENCE NUMERALS system 1
driver assistance system 2
vehicle 3
interior sensor 4a, 4b, 4c, 4d, 4e, 4f, 4g
simulation means 5
interface 6a, 6b, 6c, 6d, 6e, 6f, 6g
sensor chip 7a, 7b, 7c, 7d, 7e, 7f, 7g
test bench 8
dynamometer 9a, 9b, 9c, 9d
computing unit 10

The invention claimed is:

1. A system for testing a driver assistance system in a vehicle, wherein the driver assistance system has at least one interior sensor and is designed to process sensor signals of the at least one interior sensor, the system comprising:
   a computing unit simulating at least one physical property of an emulated driver which characterizes a physiological condition of the emulated driver, in particular the emulated driver's attentiveness, activity, fatigue, mood, state of health and/or drug influence, and is able to be detected by the at least one interior sensor such that it can generate sensor signals as a function of the at least one simulated physical property; and
   an interface which interacts with the driver assistance system such that sensor signals are provided to the driver assistance system as a function of the at least one simulated physical property.

2. The system according to claim 1, wherein the interface is a stimulation device configured to stimulate the interior sensor on the basis of the at least one simulated physical property.

3. The system according to claim 2, wherein the stimulation device is configured to generate a response signal for reception by the at least one interior sensor based on a signal emitted by the at least one interior sensor, wherein the response signal is generated based on the at least one simulated physical property, and wherein the emulated driver is emulated when generating the response signal.

4. The system according to claim 2, wherein the stimulation device is configured to be mounted on a driver's seat and/or a gear selector lever and/or steering wheel.

5. The system according to claim 1, wherein the computing unit is configured to generate raw sensor data and the interface is configured to inject the raw sensor data into a sensor chip of the interior sensor, in particular a perception chip of a camera.

6. The system according to claim 1, wherein the computing unit is configured to generate the sensor signals and the interface is configured to inject the sensor signals into the driver assistance system.

7. The system according to claim 1, wherein the at least one physical property is/are selected from among the following group of properties: biometric properties, seated position, posture, position of the head, position of the hand, viewing direction, facial expression, occluded field of view, in particular due to a hat, mask or sunglasses, weight, blood pressure, heart rate, eye movement, eyelid movement, pupil size, or driver blood alcohol concentration.

8. The system according to claim 1, wherein the at least one interior sensor is/are selected from among the following group of sensors:
    camera, in particular stereoscopic camera, infrared camera, capacitive sensor, photodiode, mechanical force sensor or resistive sensor, steering angle sensor, steering torque sensor, or microphone.

9. The system according to claim 1, wherein the system comprises a system of a test bench, particularly a vehicle test bench.

10. A method for testing a driver assistance system of a vehicle, wherein the driver assistance system has at least one interior sensor and is designed to process sensor signals of the at least one interior sensor, wherein, the method comprising:
    simulating, by a computing unit, at least one physical property of an emulated driver which characterizes a physiological condition of the emulated driver, in particular the emulated driver's attentiveness, activity, fatigue, mood, state of health, and/or drug influence, and is able to be detected by the at least one interior sensor such that that it can generate sensor signals as a function of the at least one simulated physical property and the sensor signals are provided to the driver assistance system as a function of the at least one simulated physical property.

11. The method according to claim 10, wherein simulating the emulated driver is based on recorded data of an actual person, in particular video data of the person, for which one or more physiological conditions within the data are known.

12. The method according to claim 10, wherein the at least physical property is simulated by means of a driver model which is trained on the basis of real data.

13. The method according to claim 12, wherein the driver model comprises a driver animation, in particular a 3D animation, able to emulate physiological conditions.

14. The method according to claim 10, wherein an activity of the driver assistance system is monitored and an evaluation of a function of the driver assistance system is made on the basis of the activity.

15. The method according to claim 10, wherein the at least one interior sensor is stimulated on the basis of the at least one simulated physical property such that it provides the sensor signals.

16. A vehicle comprising a system for testing a driver assistance system in a vehicle, wherein the driver assistance system has at least one interior sensor and is designed to process sensor signals of the at least one interior sensor, the system comprising:
    a computing unit simulating at least one physical property of an emulated driver which characterizes a physiological condition of the emulated driver, in particular the emulated driver's attentiveness, activity, fatigue, mood, state of health and/or drug influence, and is able to be detected by the at least one interior sensor such that it can generate sensor signals as a function of the at least one simulated physical property; and
    an interface which interacts with the driver assistance system such that sensor signals are provided to the driver assistance system as a function of the at least one simulated physical property.

* * * * *